United States Patent
Liu et al.

(10) Patent No.: US 10,016,725 B2
(45) Date of Patent: Jul. 10, 2018

(54) IONIC LIQUID FOR FORWARD OSMOSIS PROCESS AND FORWARD OSMOSIS PROCESS

(71) Applicant: INDUSTRIAL TECHNOLOGY RESEARCH INSTITUTE, Hsinchu (TW)

(72) Inventors: Po-I Liu, Kaohsiung (TW); Li-Ching Chung, Changhua (TW); Chih-Hsiang Fang, Puzi (TW); Chia-Hua Ho, Miaoli (TW); Hsin Shao, Zhubei (TW); Meng-Shun Huang, New Taipei (TW); Ren-Yang Horng, Hsinchu (TW); Teh-Ming Liang, Tainan (TW); Min-Chao Chang, Hsinchu (TW); Tsui Jung Yang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/392,281

(22) Filed: Dec. 28, 2016

(65) Prior Publication Data
US 2018/0056241 A1    Mar. 1, 2018

Related U.S. Application Data

(60) Provisional application No. 62/381,187, filed on Aug. 30, 2016.

(30) Foreign Application Priority Data

Dec. 1, 2016 (TW) ............................. 105139655 A

(51) Int. Cl.
*B01D 59/30*      (2006.01)
*B01J 43/00*      (2006.01)
(Continued)

(52) U.S. Cl.
CPC ............ *B01D 61/005* (2013.01); *C02F 1/445* (2013.01); *C07C 57/145* (2013.01);
(Continued)

(58) Field of Classification Search
CPC .. B01D 61/005; B01D 61/002; C07C 57/145; C07D 207/267; C02F 1/445; C02F 2103/08; C07F 9/5407; B01J 2219/0047
See application file for complete search history.

(56) References Cited

U.S. PATENT DOCUMENTS 3,341,580 A * 9/1967 Hechenbleikner ........ C07F 9/54
                                                        562/488
5,294,644 A * 3/1994 Login .................... A01N 25/04
                                                        504/365
(Continued)

FOREIGN PATENT DOCUMENTS

CN      101153018 A  *  4/2008
CN      101284913 A  * 10/2008
(Continued)

OTHER PUBLICATIONS

Taiwanese Notice of Allowance and Search Report for Taiwanese Application No. 105139655, dated Apr. 11, 2017.
(Continued)

*Primary Examiner* — Pamela H Weiss
(74) *Attorney, Agent, or Firm* — Birch, Stewart, Kolasch & Birch, LLP

(57) ABSTRACT

A forward osmosis process is provided, which includes separating a feed part and a draw solution part by a semi-permeable film. An ionic liquid is introduced into the draw solution part, and brine is introduced into the feed part. The brine has an osmotic pressure lower than that of the ionic liquid, so that pure water of the brine permeates through the (Continued)

semi-permeable film, enters the draw solution part, and mixes with the ionic liquid to form a draw solution. The draw solution was obtained out of the draw solution part to be left to stand at room temperature, so that the draw solution separated into a water layer and an ionic liquid layer. The ionic liquid includes

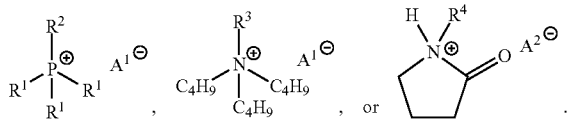

6 Claims, 5 Drawing Sheets

(51) Int. Cl.
  *C02F 1/44* (2006.01)
  *B01D 61/00* (2006.01)
  *C07C 57/145* (2006.01)
  *C07D 207/267* (2006.01)
  *C07F 9/54* (2006.01)
  *C02F 103/08* (2006.01)
(52) U.S. Cl.
  CPC ........ *C07D 207/267* (2013.01); *C07F 9/5407* (2013.01); *C02F 2103/08* (2013.01)

(56) References Cited

U.S. PATENT DOCUMENTS

| | | | | |
|---|---|---|---|---|
| 2004/0094741 | A1* | 5/2004 | Sato | ........ C07C 217/08 252/1 |
| 2006/0144789 | A1 | 7/2006 | Cath et al. | |
| 2007/0021604 | A1* | 1/2007 | Deng | ........ B01J 31/0282 540/485 |
| 2011/0140037 | A1* | 6/2011 | Lean | ........ B01D 17/0208 252/182.3 |
| 2013/0048561 | A1 | 2/2013 | Wilson et al. | |
| 2013/0240444 | A1 | 9/2013 | Jung et al. | |
| 2013/0256228 | A1 | 10/2013 | Bharwada et al. | |
| 2014/0217026 | A1 | 8/2014 | Han et al. | |
| 2015/0165380 | A1 | 6/2015 | Jung et al. | |
| 2015/0321977 | A1* | 11/2015 | Broderick | ........ C07C 5/2748 585/511 |
| 2016/0082391 | A1* | 3/2016 | Hu | ........ C02F 1/445 210/644 |

FOREIGN PATENT DOCUMENTS

| | | | | |
|---|---|---|---|---|
| JP | 2010214324 | A * | 9/2010 | ........ B01D 53/228 |
| WO | WO 2011/097727 | A1 | 8/2011 | |
| WO | WO 2013036111 | A1 * | 3/2013 | ........ B01D 61/002 |
| WO | WO 2014/175833 | A1 | 10/2014 | |
| WO | WO 2014/175834 | A1 | 10/2014 | |
| WO | WO 2014175834 | A1 * | 10/2014 | ........ C02F 1/445 |
| WO | WO 2015/147749 | A1 | 10/2015 | |
| WO | WO 2015147749 | A1 * | 10/2015 | ........ B01D 61/005 |
| WO | WO 2016/027280 | A2 | 2/2016 | |

OTHER PUBLICATIONS

Bai, H., et al, "Highly water soluble and recovered dextran coated Fe3O4 magnetic nanoparticles for brackish water desalination", Separation and Purification Technology, 2011, vol. 81, pp. 392-399.
Cai, Y., et al, "Energy-efficient desalination by forward osmosis using responsive ionic liquid draw solutes", Environ. Sci.: Water Res. Technol., 2015, vol. 1, pp. 341-347.
Cai, Y., et al, "Towards temperature driven forward osmosis desalination using Semi-IPN hydrogels as reversible draw agents", Water Research, 2013, vol. 47, pp. 3773-3781.
Li, D., et al, "Stimuli-responsive polymer hydrogels as a new class of draw agent for forward osmosis desalination", Chem. Commun., 2011, vol. 47, pp. 1710-1712.
Ling, M.M., et al, "Highly Water-Soluble Magnetic Nanoparticles as Novel Draw Solutes in Forward Osmosis for Water Reuse," Ind. Eng. Chem. Res., 2010, vol. 49, pp. 5869-5876.
Liu, W., et al, "The Physical Properties of Aqueous Solutions of the Ionic Liquid [BMIM][BF4]", J Solution Chem, 2006, vol. 35, pp. 1337-1346.
Razmjou, A., et al, "Effect of particle size on the performance of forward osmosis desalination by stimuli-responsive polymer hydrogels as a draw agent," Chemical Engineering Journal, 2013, vol. 215-216, pp. 913-920.
Sato, N., et al, "Forward osmosis using dimethyl ether as a draw solute," Desalination, 2014, vol. 349, pp. 102-105.

* cited by examiner

IONIC LIQUID FOR FORWARD OSMOSIS PROCESS AND FORWARD OSMOSIS PROCESS

CROSS REFERENCE TO RELATED APPLICATIONS

This application claims the benefit of U.S. Provisional Application No. 62/381,187 filed on Aug. 30, 2016, and claims priority from Taiwan Application Serial Number 105139655 filed on Dec. 1, 2016, the entirety of which are incorporated by reference herein.

TECHNICAL FIELD

The technical field relates to a draw solute (ionic liquid) for a forward osmosis process.

BACKGROUND

The technical principle of forward osmosis (FO) desalination process utilizes an osmosis pressure difference (between two solutions/solutes in two parts separated by a semi-permeable film) as a driving force. Water in a feed part with a lower osmosis pressure will permeate through a semi-permeable film to enter a draw solution part with a higher osmosis pressure. The mixture liquid of the water (permeating through the semi-permeable film) and the draw solution can be separated or concentrated to separate the water and the draw solution, thereby recycling the draw solution and producing pure water. In water treatment, the forward osmosis process has advantages such as low energy consumption and low film fouling ratio, which may largely enhance the function stability and cost effectiveness.

The draw solution should have the properties of (1) high osmosis pressure, (2) hydrophilicity, and (3) being easily separated from water, in which the separation of the draw solution and the water (through the semi-permeable film) and the recycling of the draw solution are critical factors of energy consumption in the forward osmosis process. Some conventional skills adopts an ionic liquid to serve as draw solute, but the draw solution (mixture liquid of the water and the ionic liquid) should be heated to 35° C. to 50° C. to separate into two layers (water layer and ionic liquid layer). Obviously, the conventional methods using the ionic liquid have the problem of energy consumption due to necessary heating.

Accordingly, a novel draw solute for the forward osmosis process is still called for to solve the problem described above.

SUMMARY

One embodiment of the disclosure provides an ionic liquid for a forward osmosis process, comprising:

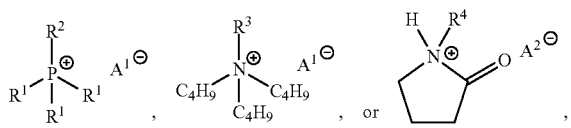

wherein $R^1$ is $C_{4-6}$ alkyl group, $R^2$ is $C_{4-14}$ alkyl group, $R^3$ is $C_{3-16}$ alkyl group, $R^4$ is $C_{1-8}$ alkyl group, $A^{1\ominus}$ is

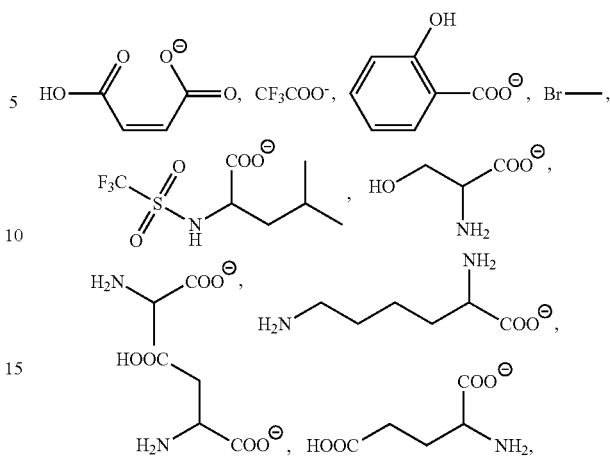

or a combination thereof, and $A^{2\ominus}$ is $HSO_4^-$, $NO_3^-$, $Cl^-$, or a combination thereof.

One embodiment of the disclosure provides a forward osmosis process, comprising: separating a feed part and a draw solution part by a semi-permeable film; introducing an ionic liquid into the draw solution part; introducing brine into the feed part, wherein the brine has an osmotic pressure lower than that of the ionic liquid, in which pure water of the brine permeates through the semi-permeable film, enters the draw solution part, and mixes with the ionic liquid to form a draw solution; and obtaining the draw solution out of the draw solution part; letting the draw solution stand at room temperature, thereby separating the draw solution into a water layer and an ionic liquid layer, wherein the ionic liquid includes

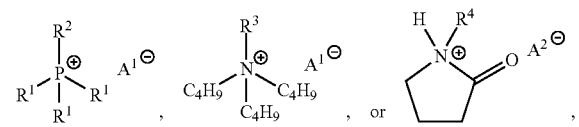

wherein $R^1$ is $C_{4-6}$ alkyl group, $R^2$ is $C_{4-14}$ alkyl group, $R^3$ is $C_{3-16}$ alkyl group, $R^4$ is $C_{1-8}$ alkyl group, $A^{1\ominus}$ is

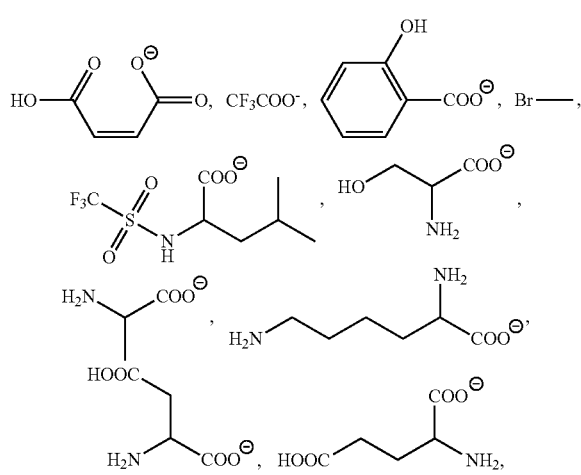

or a combination thereof, and $A^{2\ominus}$ is $HSO_4^-$, $NO_3^-$, $Cl^-$, or a combination thereof.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
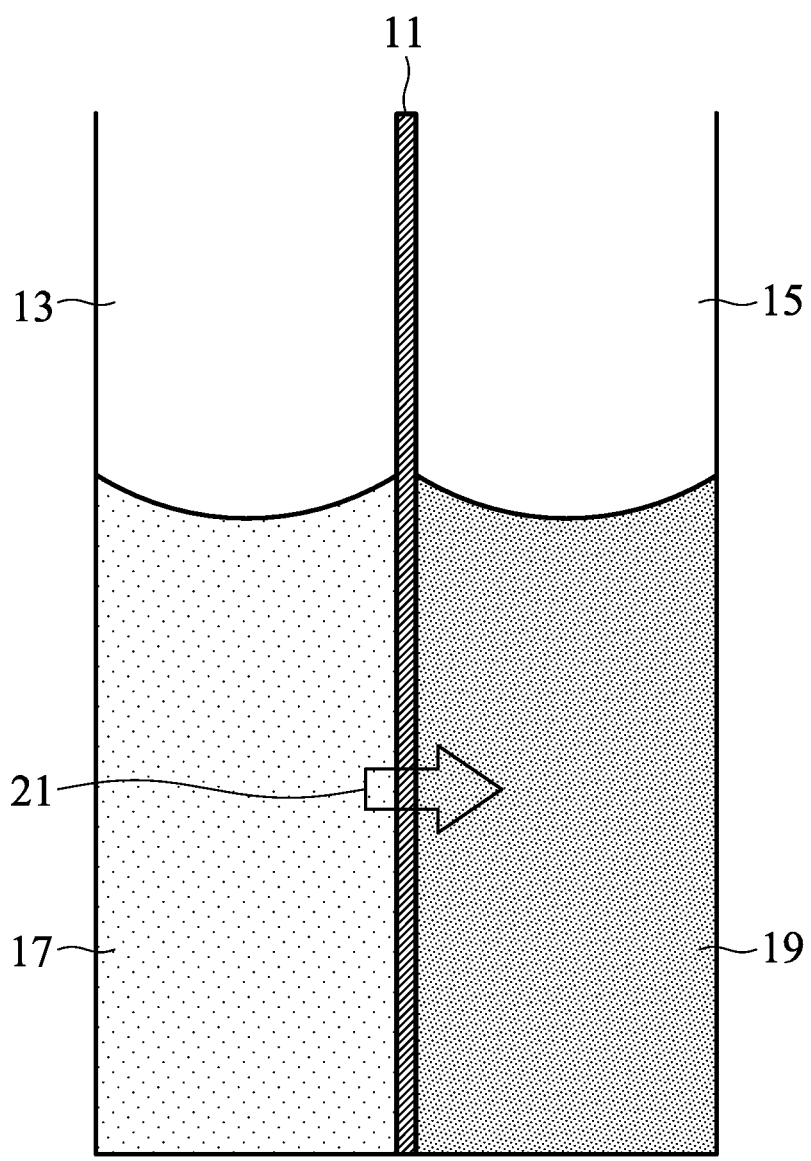
FIG. 1 shows a forward osmosis process in one embodiment of the disclosure.

In the following detailed description, for the purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

One embodiment of the disclosure provides a forward osmosis process, including separating a feed part 13 and a draw solution part 15 by a semi-permeable film 11, as shown in FIG. 1. Subsequently, brine 17 is introduced into the feed part 13, and ionic liquid 19 is introduced into the draw solution part 15. Because the osmosis pressure of the brine 17 is lower than that of the ionic liquid 19, pure water 21 of the brine 17 may permeate through the semi-permeable film 11, enter the draw solution part 15, and mix with the ionic liquid 19 to form a draw solution. In one embodiment, the draw solution can be stirred further, so that the draw solution in the draw solution part 15 will not be separated into a water layer and an ionic liquid layer. As such, the osmosis pressure of the draw solution in the draw solution part will not be influenced, and water flux will not be decreased. When the water content of the draw solution achieves a certain degree, the draw solution was then obtained out of the draw solution part 15, and then left to stand at room temperature. In one embodiment, the draw solution can be conducted to another tank for being left to stand by a pipe. Because the anion and cation of the ionic liquid in the draw solution part 15 is designed, the anion of the ionic liquid itself or a mixture liquid of the two ionic liquid has high water absorption ability due to hydrogen bonding. When the anion concentration achieves a certain range, the hydrophilicity of the anion will be reduced by conformational change such as intramolecular hydrogen bonding or the like, and the aggregation of the anion and the hydrophobic cation will increase.

As a result, the anion and the cation of the certain concentration range will aggregate, so that the standing draw solution will be separated into the water layer and the ionic liquid layer. It is not necessary to provide additional heat energy to the draw solution, and the draw solution can be spontaneously separated into the ionic liquid 19 and water.

In one embodiment, the ionic liquid layer can be reintroduced into the draw solution part 15 (e.g. recycle) after the step of separating the draw solution into the water layer and the ionic liquid layer. For example, the ionic liquid layer in the other tank can be introduced back to the draw solution part 15 by a pipe for reusing the ionic liquid. In one embodiment, the step of introducing the brine into the feed part can be continuously introducing seawater for keeping the osmosis pressure (concentration) of the brine in the feed part 13 remained unchanged. As such, the phenomenon of the pure water 21 (of the brine) permeating into the draw solution part 15 will not increase the concentration and the osmosis pressure of the brine 17 in the feed part 13, and the flux of the pure water 21 permeating into the draw solution part 15 is not decreased. Alternatively, the brine can be waste water from a factory, a house, or a laboratory.

In one embodiment, the ionic liquid layer and the water layer have a weight ratio of 10:90 to 50:50 in the step of separating the draw solution into the water layer and the ionic liquid layer. If the weight ratio of the ionic liquid in the draw solution is too high or too low, the draw solution cannot be separated into the ionic liquid layer and the water layer at room temperature. In one embodiment, the room temperature is between 15° C. to 30° C. If the draw solution containing an ionic liquid with the phase separation property needs an overly high temperature (e.g. higher than room temperature) to be separated into two layers, it should be heated further for the separation. However, the additional heating step will consume more energy.

The ionic liquid includes

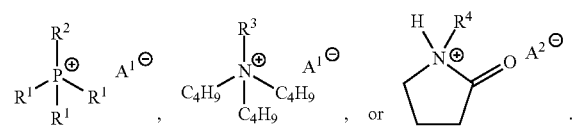

$R^1$ is $C_{4-6}$ alkyl group, $R^2$ is $C_{4-14}$ alkyl group, $R^3$ is $C_{3-16}$ alkyl group, and $R^4$ is $C_{1-8}$ alkyl group. $A^{2\ominus}$ is

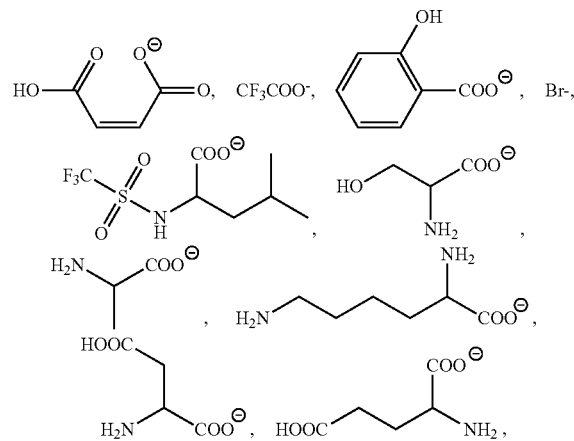

or a combination thereof. $A^{2\ominus}$ is $HSO_4^-$, $NO_3^-$, $Cl^-$, or a combination thereof. In one embodiment, $A^{1\ominus}$ is a combination of two of

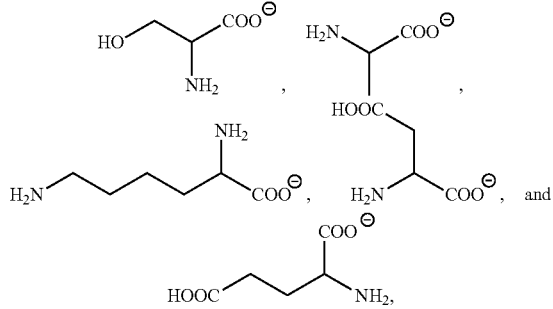

and one and another one of $A^{1\ominus}$ have a molar ratio of 1:0.2 to 1:1.

In one embodiment, the ionic liquid is

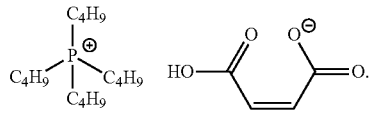

In this embodiment, the ionic liquid layer and the water layer have a weight ratio of 30:70 to 50:50 in the step of separating the draw solution into the water layer and the ionic liquid layer.

Alternatively, the ionic liquid is

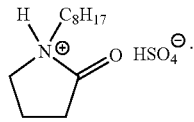

In this embodiment, the ionic liquid layer and the water layer have a weight ratio of 10:90 to 40:60 in the step of separating the draw solution into the water layer and the ionic liquid layer.

Accordingly, the ionic liquids with the specific structures serve as a draw solute in the disclosure, which may draw pure water from the brine. After being stood at room temperature, the mixture liquid (of the ionic liquid and water in specific ratios) will be spontaneously separated into two layers without being heated further. It may efficiently reduce the energy consumption of separating the draw solute and the water in the forward osmosis process.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

1 part by mole of tetrabutylphosphonium hydroxide was mixed with 1 part by mole of maleic acid, and then stirred at room temperature to be reacted for 24 hours. The resulting product was extracted with dichloromethane to collect an organic layer of the extraction. The organic layer was concentrated, and then distilled under reduced pressure to remove residual water, thereby obtaining ionic liquid [P$_{4444}$][Mal]. The above reaction is shown below:

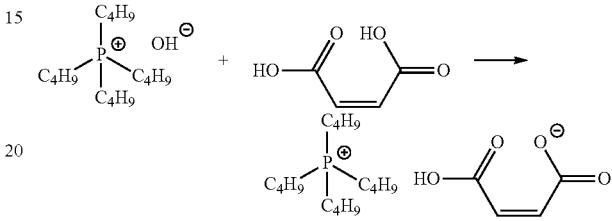

Different weight ratios of the ionic liquid [P$_{4444}$][Mal] were mixed with water, and then stood at room temperature for a while to check whether phase separation occurred in the mixture liquids or not, as tabulated in Table 1. The mixture liquid of the ionic liquid [P$_{4444}$][Mal] and water had concentration-sensitized phase-separation properties. The mixture liquid containing the ionic liquid [P$_{4444}$][Mal] of 60 wt % to 70 wt % was a homogeneous solution. When the water amount was increased to dilute the mixture liquid, such as the mixture liquid containing the ionic liquid [P$_{4444}$][Mal] of 30 wt % to 50 wt %, the mixture liquid separated into two layers. This separation was a spontaneous phase separation, and it is unnecessary to provide additional heat energy to the mixture liquid. When the water amount was increased further to dilute the mixture liquid, such as the mixture liquid containing the ionic liquid [P$_{4444}$][Mal] of 20 wt % or less, the ionic liquid and water were mixed rather than the phase separated.

TABLE 1

(Phase separation of the ionic liquid [P4444][Mal] in different concentrations)

| | Ionic liquid concentration (wt %) | | | | | | |
|---|---|---|---|---|---|---|---|
| | 10 | 20 | 30 | 40 | 50 | 60 | 70 |
| Phase separation | No | No | Yes | Yes | Yes | No | No |

The osmosis pressure of the ionic liquid ionic liquid [P$_{4444}$][Mal] was analyzed by a freezing point depression method through an instrument OSMOMAT 030 (commercially available from GONOTEC). The principle of the freezing point depression method is measuring the freezing point of a solution of the ionic liquid. If one mole of a solute (e.g. ionic liquid) could lower the freezing point of one kilogram of water (containing the solute) by 1.86° C., the osmosis pressure of the solute can be defined as 1 Osmol/kg.

Figure 2:
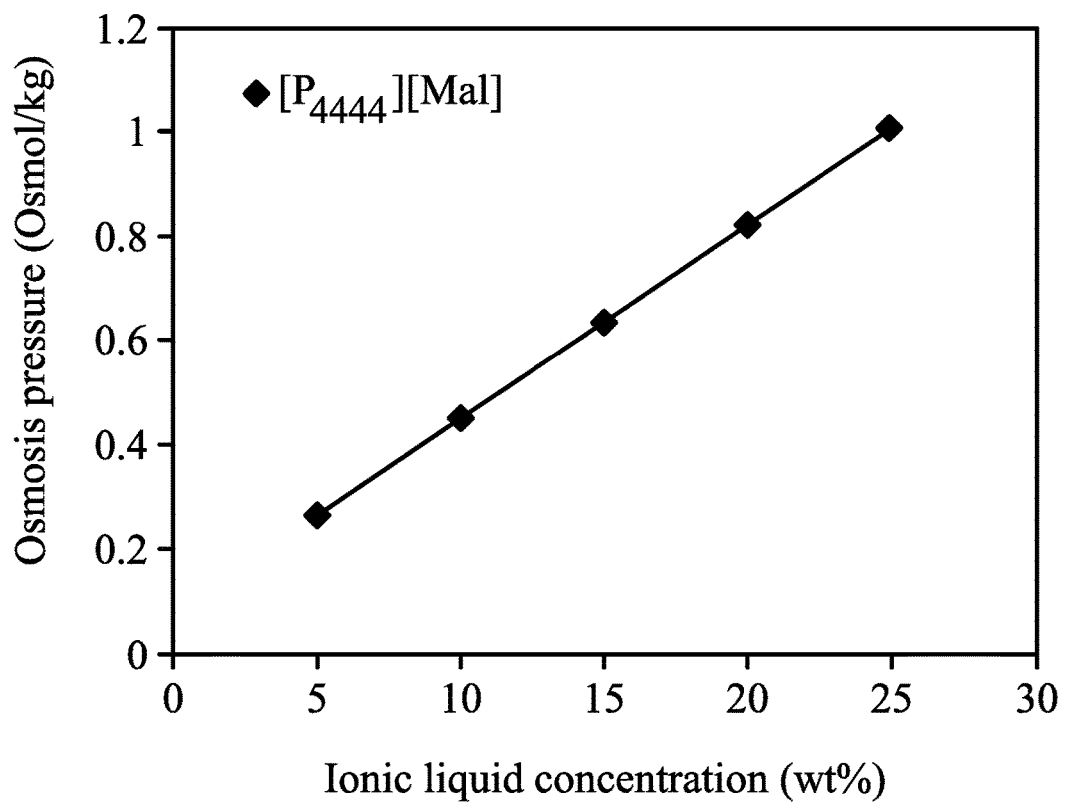
FIG. 2 shows the relationship between ionic liquid concentrations and the osmosis pressures of a mixture liquid in one embodiment of the disclosure.

As shown in experimental results, when the concentrations of the ionic liquid [P$_{4444}$][Mal] ranged between 5 wt % to 25 wt %, the osmosis pressure of the mixture liquid (containing the ionic liquid [P$_{4444}$][Mal] and water) increased linearly as the ionic liquid concentration increased, as shown in FIG. 2. When the concentration of the ionic liquid [P$_{4444}$][Mal] achieved 25 wt %, the mixture liquid containing the ionic liquid and water had an osmosis pressure of 1.0 Osmol/kg (close to that of seawater, 1.2 Osmol/kg).

In addition, the osmosis pressure of a mixture liquid containing the ionic liquid [P$_{4444}$][Mal] of high concentration was beyond the instrument detection limit. As such, the equation of the osmosis pressure versus the ionic liquid [P$_{4444}$][Mal] concentration (5 wt % to 25 wt %) of the mixture liquid was derived from measured data. Subsequently, the osmosis pressure of the mixture liquid containing a different ionic liquid [P$_{4444}$][Mal] concentration (30 wt % to 70 wt %) was estimated by the equation, as tabulated in Table 2. The mixture liquid containing the ionic liquid [P$_{4444}$][Mal] concentration of 30 wt % to 70 wt % had high osmosis pressures, e.g. two to five times the osmosis pressure of seawater.

TABLE 2

| | Ionic liquid [P4444][Mal] concentration | | | | |
|---|---|---|---|---|---|
| | 30 wt % | 40 wt % | 50 wt % | 60 wt % | 70 wt % |
| Osmosis pressure of the mixture liquid (Osmol/Kg) | 1.3 | 1.9 | 2.8 | 4.1 | 6.3 |

* The osmosis pressure of seawater (e.g. 0.6M NaCl) was 1.2 Osmol/kg.

Figure 3:
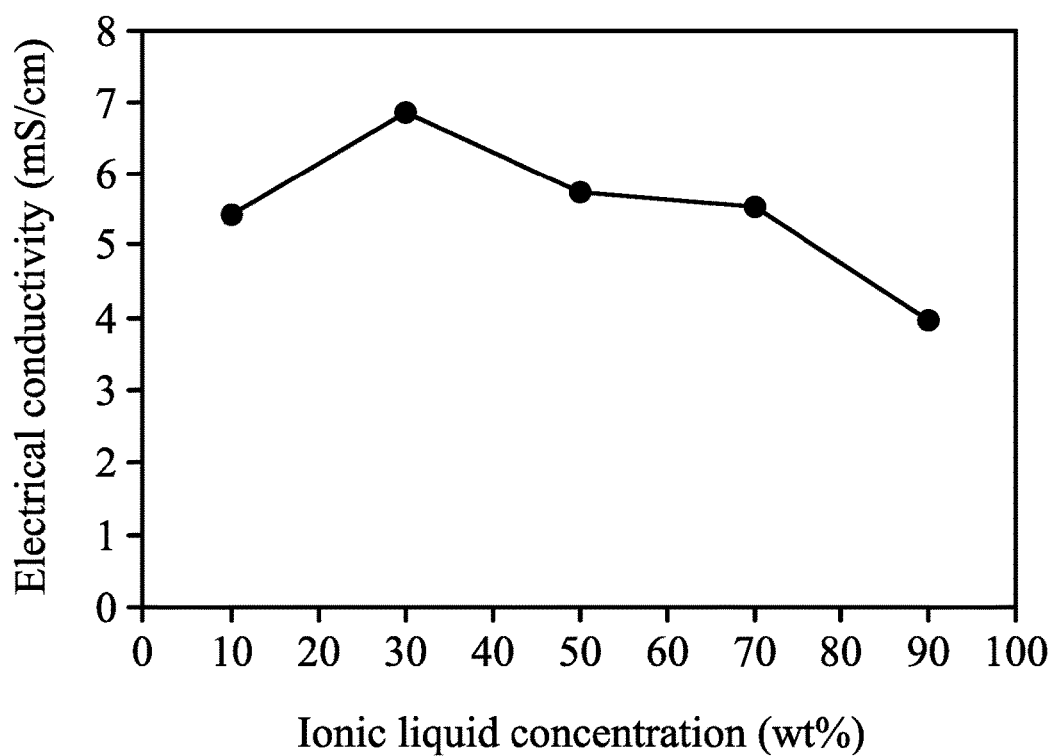
FIG. 3 shows the relationship between ionic liquid concentrations and the electrical conductivities of a mixture liquid in one embodiment of the disclosure.

The relation of ionic liquid concentration versus electrical conductivity of the mixture liquid (containing the ionic liquid [P$_{4444}$][Mal] of different concentrations) is shown in FIG. 3. The mixture liquid containing high ionic liquid concentration had an initial electrical conductivity of about 4 mS/cm, and the electrical conductivity increased as the water content increased. The ionic liquid in the ionic liquid-rich region existed as a type of ion pair, and the self-aggregation phenomenon of the ionic liquid was reduced by the water content increase, so that the ion pairs will be separated into individual anions and cations. By the ionic liquid properties, the forward osmosis process can be stably operated with a high water flux. Moreover, the forward osmosis process utilizing the ionic liquid has better performance than other forward osmosis processes utilizing inorganic salt as draw solute.

Figure 4:
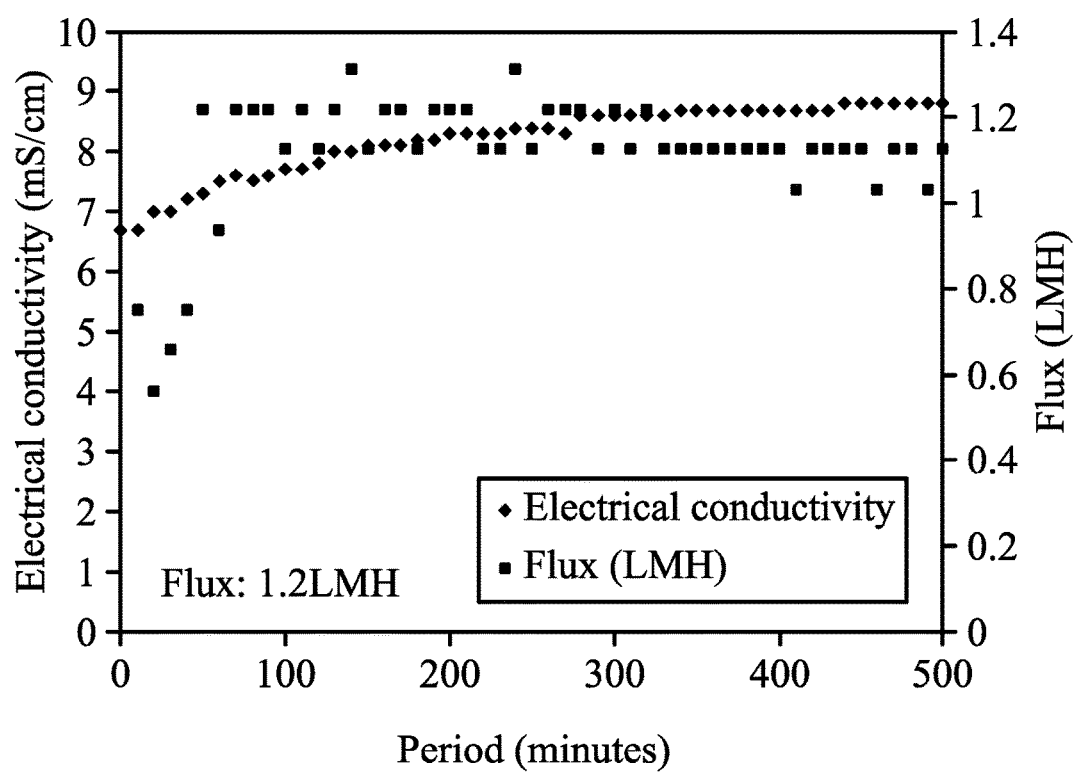
FIG. 4 shows the relationship between weight changes of the feed part and the draw solution part (water flux) and the periods, and the relationship between electrical conductivities of a draw solution in the draw solution part and the periods in one embodiment of the disclosure.

A forward osmosis device was assembled in the laboratory. A forward osmosis module was plate type. A flow channel design was dual-channel circulation type. A film was TW30-1812 with an effective area of 64 cm² (commercially available from Dow-filmtec Co.) to separate a feed part and a draw solution part. Solutions were respectively introduced into the feed part and draw solution part by a pump. The weight of the feed part and the weight of the draw solution part in different time points were measured by scan rate of 25 cm/s and recorded. The water flux was calculated by the weight change, the film area, and the experiment period, as shown in FIG. 4.

The ionic liquid [P$_{4444}$][Mal] was introduced to the draw solution part, and de-ionized water was introduced into the feed part. In an initial stage, the electrical conductivity of the mixture liquid in the draw solution part and the water flux increased as the experiment period increased. After being stably operated for 8 hours, the water flux and the electrical conductivity of the mixture liquid in the draw solution part were still maintained. It proves that the ionic liquid [P$_{4444}$]

[Mal] serving as the draw solute of the forward osmosis process has an advantage such as stable operation.

Example 2

1 part by mole of N-octyl pyrrolidone was mixed with 1 part by mole of sulfuric acid in ice bath, and then reacted for 24 hours to obtain ionic liquid [HNOP][HSO$_4$]. The above reaction is shown below:

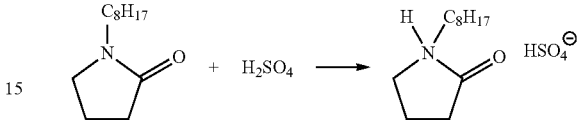

Different weight ratios of the ionic liquid [HNOP][HSO$_4$] were mixed with water, and then stood at room temperature for a while to check whether phase separation occurred in the mixture liquids or not, as tabulated in Table 3. The mixture liquid of the ionic liquid [HNOP][HSO$_4$] and water had concentration-sensitized phase-separation properties. The mixture liquid containing the ionic liquid [HNOP][HSO$_4$] of 50 wt % to 70 wt % was a homogeneous solution. When the water amount was increased to dilute the mixture liquid, such as the mixture liquid containing the ionic liquid [P$_{4444}$][Mal] of 40 wt % or less, the mixture liquid separated into two layers. This separation was a spontaneous phase separation, and it is unnecessary to provide additional heat energy to the mixture liquid.

TABLE 3

(Phase separation of the ionic liquid [HNOP][HSO$_4$] in different concentrations)

| | Ionic liquid concentration (wt %) | | | | | | |
|---|---|---|---|---|---|---|---|
| | 0 | 20 | 30 | 40 | 50 | 60 | 70 |
| Phase separation | Yes | Yes | Yes | Yes | No | No | No |

Comparative Example 1

Different weight ratios of the ionic liquid [P$_{4444}$][Mal] prepared in Example 1 were respectively mixed with water at a low temperature (close to 10° C.) to form homogeneous solutions containing the ionic liquid [P$_{4444}$][Mal] of 10 wt %, 30 wt %, 50 wt %, and 70 wt %. The homogeneous solutions were slowly heated to observe the phase separation temperature thereof, as shown in FIG. 5.

Different weight ratios of the ionic liquid [P$_{4444}$][TSO] (#86933, commercially available from Aldrich) were respectively mixed with water at a low temperature (close to 10° C.) to form homogeneous solutions containing the ionic liquid [P$_{4444}$][TSO] of 10 wt %, 30 wt %, and 50 wt %. The homogeneous solutions were slowly heated to observe the phase separation temperature thereof, as shown in FIG. 5.

Figure 5:
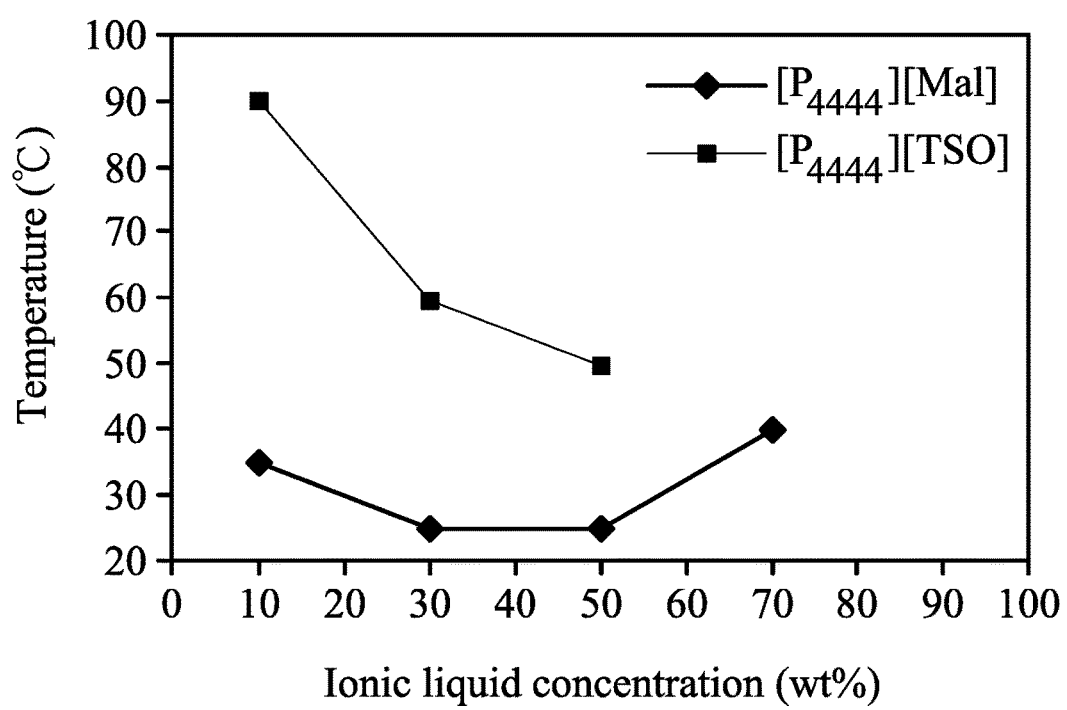
FIG. 5 shows the relationship between phase separation temperatures and ionic liquid concentrations of mixture liquids containing different ionic liquids in one embodiment of the disclosure.

As shown in FIG. 5, the mixture liquids containing the ionic liquid [P$_{4444}$][Mal] of 30 wt % to 50 wt % separated into two layers at room temperature, and all the mixture liquids containing the ionic liquid [P$_{4444}$][TSO] separated into two layers at a temperature higher than room temperature. Compared to the ionic liquid [P$_{4444}$][TSO], the mixture liquid of water and the ionic liquid [P$_{4444}$][Mal] in the forward osmosis process can separate into two layers without heating, which may save the heat energy for separating the draw solute and water in the forward osmosis process.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. A forward osmosis process, comprising:
   separating a feed part and a draw solution part by a semi-permeable film;
   introducing an ionic liquid into the draw solution part;
   introducing brine into the feed part, wherein the brine has an osmotic pressure lower than that of the ionic liquid, in which pure water of the brine permeates through the semi-permeable film, enters the draw solution part, and mixes with the ionic liquid to form a draw solution; and
   obtaining the draw solution out of the draw solution part;
   letting the draw solution stand at room temperature, thereby the draw solution separating into a water layer and an ionic liquid layer, wherein room temperature ranges between 15° C. to 30° C., and wherein the ionic liquid is

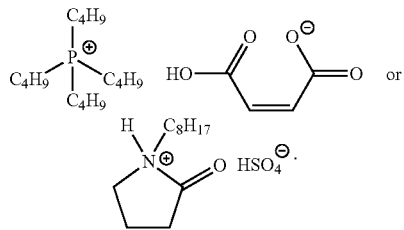

2. The forward osmosis process as claimed in claim 1, wherein the ionic liquid is

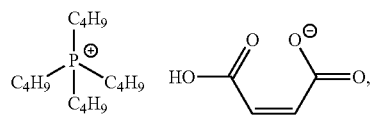

and the ionic liquid layer and the water layer have a weight ratio of 30:70 to 50:50 in the step of separating the draw solution into the water layer and the ionic liquid layer.

3. The forward osmosis process as claimed in claim 1, wherein the ionic liquid is

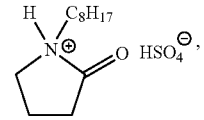

and the ionic liquid layer and the water layer have a weight ratio of 10:90 to 40:60 in the step of separating the draw solution into the water layer and the ionic liquid layer.

4. The forward osmosis process as claimed in claim 1, further comprising introducing the ionic liquid layer into the draw solution part after the step of separating the draw solution into the water layer and the ionic liquid layer.

5. The forward osmosis process as claimed in claim 1, wherein the step of introducing the brine into the feed part is continuously introducing seawater into the feed part.

6. The forward osmosis process as claimed in claim 1, further comprising a step of stirring the pure water and the ionic liquid in the draw solution part for mixing the pure water and the ionic liquid to form the draw solution.

* * * * *